United States Patent [19]

Hofmann

[11] Patent Number: Plant 7,085

[45] Date of Patent: Dec. 26, 1989

[54] DISTINCT VARIETY OF GERANIUM PLANT NAMED CHERRY

[75] Inventor: Christa Hofmann, Dresden, German Democratic Rep.

[73] Assignee: Oglevee Ltd., Connellsville, Pa.

[21] Appl. No.: 298,509

[22] Filed: Jan. 18, 1989

[51] Int. Cl.[4] ..... A01H 5/00
[52] U.S. Cl. ..... Plt./68
[58] Field of Search ..... Plt./68

*Primary Examiner*—James R. Feyrer
*Attorney, Agent, or Firm*—Webb, Burden, Ziesenheim & Webb

[57] ABSTRACT

A new cultivar is characterized by its compact, well branched, upright plant that provides a neat habit. The bright fluorescent crimson to ruby red color of the bloom accents the dark green foliage. The plant has shown good outdoor performance that equals or in some cases surpasses the variety Veronica.

1 Drawing Sheet

BACKGROUND OF THE NEW PLANT

The present invention comprises a new and distinct cultivar of *Pelargonium hortorum* bailey known by the varietal name of Cherry. The new variety was discovered in a selected breeding program by Mrs. Christa Hofmann and is a selection from the crossing of Veronica, U.S. Plant Pat. No. 5,054, formerly known as Purpurball and the mixed pistils of small i-lines in the colors purple and carmine.

The new cultivar was discovered in the year 1984 at the VEB Saatyucht Zierpflanzen, Dresden, German Democratic Republic; it was first asexually reproduced by cuttings in Dresden, Germany Democratic Republic and has been repeatedly asexually reproduced by cuttings over a two year period for Oglevee Associates, Inc., in Connellsville, Pa. It has also been trial and field tested over the summers of 1987 and 1988 in Connellsville, Pa. and has been found to retain its distinctive characteristics throughout successive propagation.

The new cultivar, when grown in a greenhouse in Connellsville, Pa. using natural light, 60° Fahrenheit night temperature, 68° Fahrenheit day temperature and 71° Fahrenheit vent temperature has a response time of six weeks from a well rooted cutting to a flowering plant in a 4 inch (10 cm.) pot.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out for Oglevee Associates, Inc. in Connellsville, Pa. The plant history was taken on six week plants in which rooted cuttings were potted on Aug. 1, 1988 and subsequently flowered on Sept. 15, 1988. The plants were blossomed under natural light in a greenhouse and the color readings were taken under 200–220 foot candles of cool, white fluorescent light. The cuttings were grown in a soilless media and received constant fertilizer of 250–300 parts per million nitrogen and potassium. Color references are primarily to the R.H.S. Colour Chart of The Royal Horticultural Society of London.

THE PLANT

Classification:
- *Botanical.*—*Pelargonium* × *hortorum* bailey.
- *Commercial.*—Zonal geranium.

Form: Semi-dwarf; compact growth; free basal branching; free and early flowering; upright habit.
Height: 20–25 cm. from the media surface.
Growth: Short internodes; free branching from base.
Strength: Stands upright without artificial support.
Foliage: No zoning; stalked leaf attachment.
Leaves:
- *Size.*—6 to 8 cm. across.
- *Shape.*—Reniform; cordate base.
- *Margin.*—Crenate.
- *Texture.*—Pubescent; dull (not reflective).
- *Color.*—Top: Green Group 137B. Bottom: Yellow-green Group 146B.
- *Ribs and veins.*—Palmate veination; Yellow-green Group 145B.

Petioles: 5–8 cm. in length; Yellow-green Group 146B.
Stem:
- *Color.*—Yellow-green Group 144A.
- *Internodes.*—1–2 cm. in length.

THE BUD

Shape: Upright; hemispherical cluster.
Size: 1.5–2.5 cm. across.

INFLORESCENCE

Blooming habit: Continuous; upright; semi-double; hemispherical; slow to shatter.
Size: 9–12 cm.
Borne: Umbel; 4–7 cm. above foliage; florets on pedicel; pedicel on peduncle.
Florets:
- *Form.*—Flat to slightly cupped; obovate.
- *Color.*—Top: Red-purple Group 57A. Bottom: Red-purple Group 58B.
- *Petals.*—7–9 in number; separate; not united; margin entire; smooth; flat to slightly cupped.
- *Size.*—2.5–3.5 cm. across
- *Texture and appearance.*—Smooth; color from a distance appears fluorescent.

Petaloids:

*Quantity.*—0–3.

*Shape.*—Narrow; elongated; twisted.

*Color.*—Top: Red-purple Group 66B. Bottom: Red-purple Group 66C.

Pedicel: 2.5–3 cm. in length. Red-purple Group 59B.

Peduncle: Arises from node opposite leaf petiole; 14–16 cm. in length.

*Color.*—Yellow-green Group 146A.

*Tonality.*—Crimson to ruby red (Exotica Horticultural Color Guide).

REPRODUCTIVE ORGANS

Stamens:

*Anthers.*—1–2 mm. in length.

*Filaments.*—White at base to pink at tip; irregular in shape; flat; 0.5–0.7 cm. in length.

*Pollen.*—Golden yellow.

Pistils:

*Number.*—1 with 5 part stigma.

*Length.* 8–9 mm.

*Stigma.*—1; 5 parted at maturity; Red-purple Group.

*Style.*—3–4 mm. in length; white to pale green.

Ovaries: 2–3 mm. in length; 1–2 mm. across; very pubescent; pale green; superior.

The new cultivar is characterized by its compact, well branched, upright plant that provides a neat habit. The bright fluorescent crimson to ruby red color of the bloom accents the dark green foliage. The plant has shown good outdoor performance that equals or in some cases surpasses the variety Veronica.

I claim:

1. A new and distinct variety of geranium plant characterized by a bright, fluorescent, crimson to ruby red color accented by dark green foliage, compact, well branched and upright plant and good outdoor performances as herein shown and described.

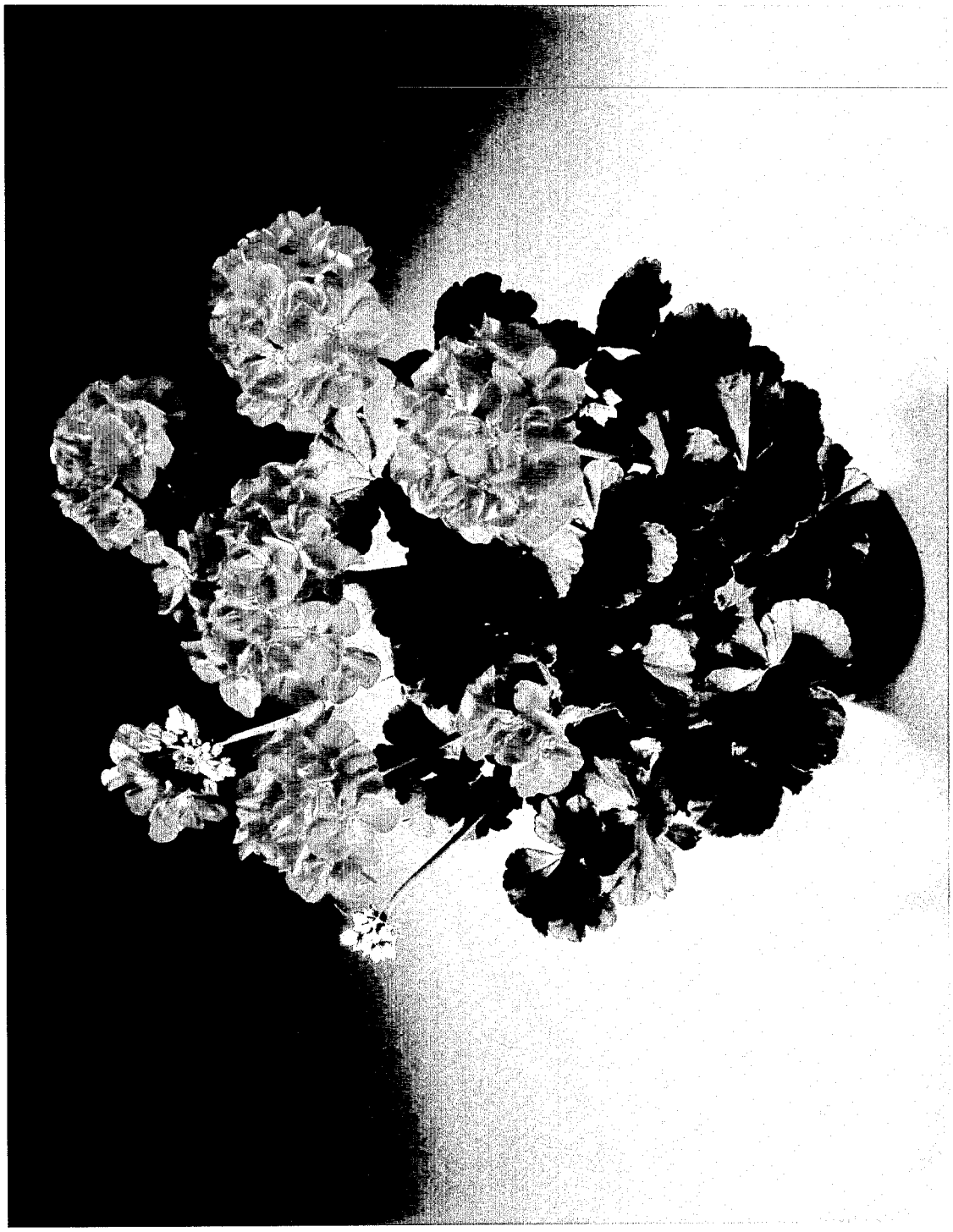

* * * * *